(12) United States Patent  
Kendrick et al.

(10) Patent No.: US 7,835,557 B2
(45) Date of Patent: Nov. 16, 2010

(54) SYSTEM AND METHOD FOR DETECTING STATUS OF IMAGING DEVICE

(75) Inventors: Lance Kendrick, Lafayette, CO (US); Andrew Bzostek, Erie, CO (US); Dave Becker, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1023 days.

(21) Appl. No.: 11/605,771

(22) Filed: Nov. 28, 2006

(65) Prior Publication Data

US 2008/0123820 A1    May 29, 2008

(51) Int. Cl.
*G06K 9/00* (2006.01)

(52) U.S. Cl. .................. 382/128; 382/132; 382/283; 600/407

(58) Field of Classification Search ............... 382/128, 382/132, 276, 282, 283, 287; 600/407
See application file for complete search history.

(56) References Cited

U.S. PATENT DOCUMENTS

| 5,592,939 | A | 1/1997 | Martinelli |
| 5,740,808 | A | 4/1998 | Panescu et al. |
| 5,913,820 | A | 6/1999 | Bladen et al. |
| 5,983,126 | A | 11/1999 | Wittkampf et al. |
| 6,377,656 | B1 | 4/2002 | Ueki et al. |
| 6,381,485 | B1 | 4/2002 | Hunter et al. |
| 6,474,341 | B1 | 11/2002 | Hunter et al. |
| 7,006,600 | B1 * | 2/2006 | Krema et al. ............... 378/98.7 |
| 7,355,183 | B2 * | 4/2008 | Spahn .................... 250/370.09 |
| 2004/0062439 | A1 * | 4/2004 | Cahill et al. ................. 382/173 |
| 2004/0215071 | A1 | 10/2004 | Frank et al. |
| 2005/0033117 | A1 | 2/2005 | Ozaki et al. |
| 2005/0085714 | A1 | 4/2005 | Foley et al. |
| 2005/0085720 | A1 | 4/2005 | Jascob et al. |
| 2005/0161610 | A1 | 7/2005 | Spahn |
| 2006/0247521 | A1 * | 11/2006 | McGee ........................ 600/434 |
| 2008/0021300 | A1 * | 1/2008 | Allison ........................ 600/407 |

FOREIGN PATENT DOCUMENTS

WO    WO-0169534    9/2001

OTHER PUBLICATIONS

International Search Report and Written Opinion for PCT/US2007/024493 mailed Jul. 2, 2008.

* cited by examiner

*Primary Examiner*—John B Strege
(74) *Attorney, Agent, or Firm*—Harness, Dickey (57) ABSTRACT

A system for detecting a status of an imaging device for use with a surgical navigation system is provided. The system can comprise a source of at least one image and a mask module that generates a mask array for each received image. The system can also include a background check module that determines a content of the image defined by the mask array and a radiation status module that determines a status of the imaging device based on the content of the image.

30 Claims, 8 Drawing Sheets

SYSTEM AND METHOD FOR DETECTING STATUS OF IMAGING DEVICE

FIELD

The present disclosure relates generally to navigated surgery, and more specifically, to systems and methods for detecting an operational status of an imaging device.

BACKGROUND

The statements in this section merely provide background information related to the present disclosure and may not constitute prior art.

Image guided medical and surgical procedures utilize patient images obtained prior to or during a medical procedure to guide a physician performing the procedure. Recent advances in imaging technology, especially in imaging technologies that produce highly-detailed, two, three, and four dimensional images, such as computed tomography (CT), magnetic resonance imaging (MRI), fluoroscopic imaging (such as with a C-arm device), positron emission tomography (PET), and ultrasound imaging (US) has increased the interest in image guided medical procedures.

Typical image guided navigation systems generally require dynamic reference frames to track the position of the patient should patient movement occur during the assisted procedure. The dynamic reference frame is generally affixed to the patient in a generally permanent or immovable fashion. The dynamic reference frame may also be used as a fiducial marker and may, therefore, be attached to the patient during the acquisition of pre-operative images. This enables the image space to be aligned with patient space during the navigated procedure. Generally, during the navigated procedure, images are taken by a suitable imaging device to update the patient space (in the case of patient movement) and/or update the tracking of a navigated instrument.

In order to properly correlate the intra-operative images with the pre-operative images, the navigation system needs to be aware of the activation and deactivation of the imaging device. For example, in the case of a fluoroscopic C-arm x-ray imaging system, radiation sensors can be used to determine if the C-arm is actively imaging. The use of radiation sensors can be undesirable in cases where large bodies absorb the radiation generated by the C-arm, and thereby inhibit detection of the generated radiation by the radiation sensors. Accordingly, it can be desirable to provide a system and method for detecting the operational status of the imaging device.

SUMMARY

A system for detecting a status of an imaging device for use with a surgical navigation system. The system can comprise a source of at least one image and a mask module that generates a mask array for each received image. The system can also include a background check module that determines a content of the image defined by the mask array and a radiation status module that determines the status of the imaging device based on the content of the image.

Provided is a method of detecting a status of an imaging device for use with a surgical navigation system. The method includes providing a source of at least one image and generating a mask for the image, with the mask defining a background area of the image. The method also includes determining a content of the background area of the image and determining, based on the background area of the image, the status of the imaging device.

A method of tracking a portion of an anatomy is further provided. The method can include providing an imaging device and coupling a tracking device to at least one of the anatomy or an instrument. The method can also include tracking the tracking device relative to the anatomy and generating at least one image. The method can include generating a mask for the image, with the mask defining a background of the image, and detecting a content of non-black pixels in a background of the image. The method can further include determining a status of the imaging device based on the content of non-black pixels in the background and the imaging device.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing an improved system and method for detecting the status of an imaging device for use with a navigated surgical procedure. It should be noted, however, that the present teachings could be applicable to any appropriate procedure in which the operational status of an imaging device must be detected. Further, as used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality. Therefore, it will be understood that the following discussions are not intended to limit the scope of the appended claims.

Figure 1:
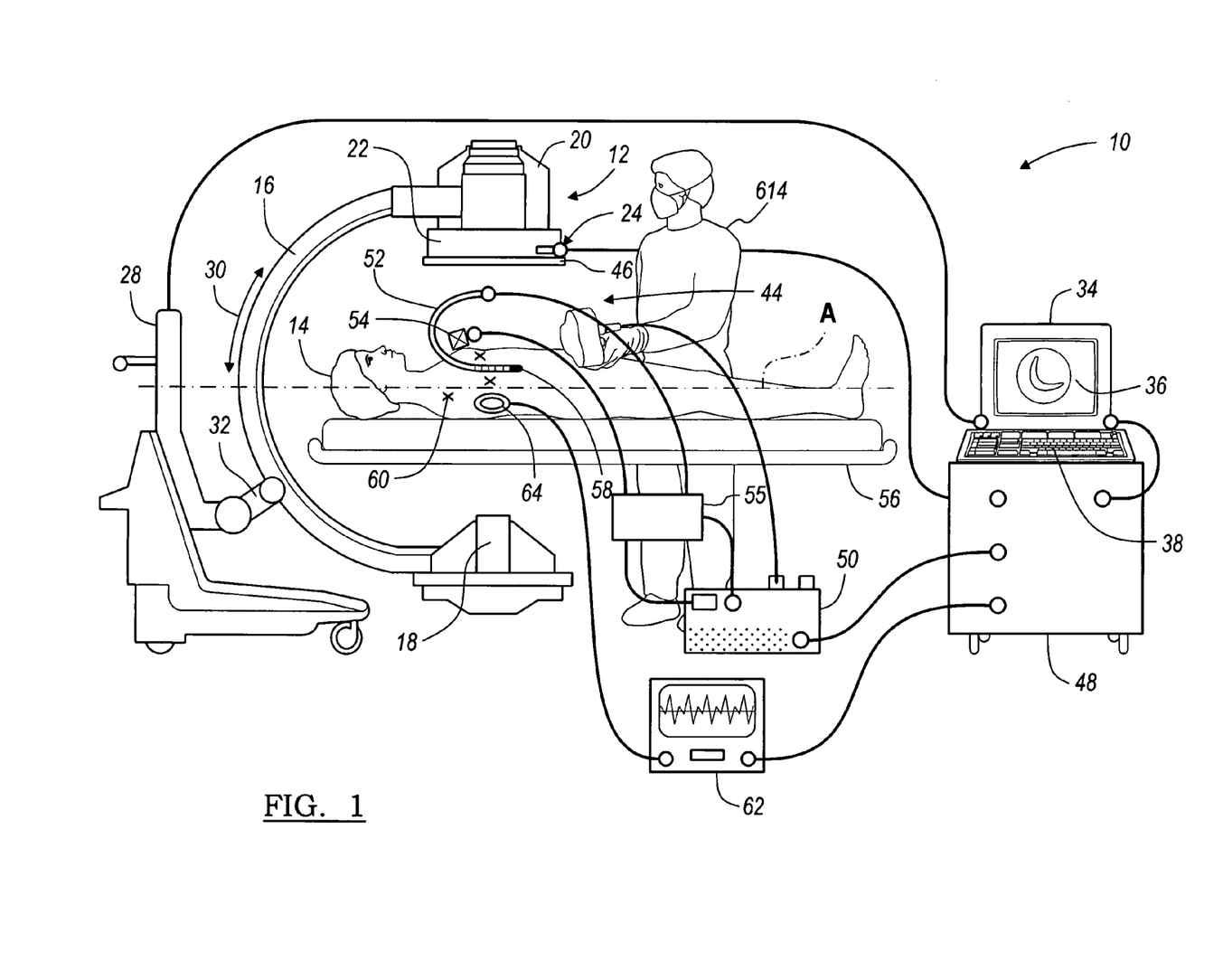
FIG. 1 is a diagram of a navigation system according to various embodiments of the present disclosure.

FIG. 1 is a diagram illustrating an overview of an image-guided navigation system 10 that can be used for various procedures. The navigation system 10 can be used to track the location of an implant, such as a spinal implant or orthopedic implant, relative to a patient 14. Also the navigation system 10 can track the position and orientation of various instruments. It should further be noted that the navigation system 10 may be used to navigate any type of instrument, implant, or delivery system, including: guide wires, arthroscopic systems, orthopedic implants, spinal implants, etc. Moreover, these instruments may be used to navigate or map any region of the body. The navigation system 10 and the various instruments may be used in any appropriate procedure, such as one that is generally minimally invasive or an open procedure.

The navigation system 10 may include an imaging device 12 that is used to acquire pre-, intra-, or post-operative or real-time image data of a patient 14. Alternatively various imageless systems can be used or images from atlas models can be used to produce patient images, such as those disclosed in U.S. Patent Pub. No. 2005-0085714, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The imaging device 12 is, for example, a fluoroscopic x-ray imaging device that may be configured as an O-arm™ or a C-arm 16 having an x-ray source 18, an x-ray receiving section 20, an optional calibration and tracking target 22 and optional radiation sensors 24.

Image data may also be acquired using other imaging devices, such as those discussed above and herein. An imaging device controller 28, that may control the C-arm 16, can capture the x-ray images received at the receiving section 20 and store the images for later use. The controller 28 may also be separate from the C-arm 16 and/or control the rotation of the C-arm 16. For example, the C-arm 16 can move in the direction of arrow 30 or rotate about a longitudinal axis 14*a* of the patient 14, allowing anterior or lateral views of the patient 14 to be imaged. Each of these movements involves rotation about a mechanical axis 32 of the C-arm 16.

In the example of FIG. 1, the longitudinal axis 14*a* of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc. An exemplary O-arm™ imaging device is available from Breakaway Imaging, LLC of Littleton, Mass.

In operation, the imaging device 12 generates x-rays from the x-ray source 18 that propagate through the patient 14 and calibration and/or tracking target 22, into the x-ray receiving section 20. It will be understood that the tracking target need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data. Receiving section 20 may also be a digital device that converts x-rays directly to digital image data for forming images, thus potentially avoiding distortion introduced by first converting to visible light. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the imaging device 12 are captured and stored in the controller 28. Multiple two-dimensional images taken by the imaging device 12 may also be captured and assembled to provide a larger view or image of a whole region of a patient, as opposed to being directed to only a portion of a region of the patient 14. For example, multiple image data of a patient's leg may be appended together to provide a full view or complete set of image data of the leg that can be later used to follow contrast agent, such as Bolus tracking.

The image data is then forwarded from the controller 28 to a navigation computer and/or processor, controller or workstation 34 having a display 36 and a user interface 38. It will also be understood that the image data is not necessarily first retained in the controller 28, but may also be directly transmitted to the workstation 34. The workstation 34 provides facilities for displaying the image data as an image on the display 36, saving, digitally manipulating, or printing a hard copy image of the of the received image data. The user interface 38 can comprise any device, such as an user input device 38*a*, that can enable a user to interface with the workstation 34, such as a touchpad, touch pen, touch screen, keyboard, mouse, wireless mouse, or a combination thereof. The user interface 38 can allow a physician or user to provide inputs to control the imaging device 12, via the C-arm controller 28, or adjust the display settings of the display 36. The workstation 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, a radiation status control module 24 identifies whether or not the imaging device 12 is actively imaging, as will be discussed in greater detail herein. This information is also transmitted to a coil array controller 48, further discussed herein.

While the imaging device 12 is shown in FIG. 1, any other alternative 2D, 3D or 4D imaging modality may also be used. For example, any 2D, 3D or 4D imaging device, such as an O-arm imaging device, isocentric fluoroscopy, bi-plane fluoroscopy, ultrasound, computed tomography (CT), multi-slice computed tomography (MSCT), magnetic resonance imaging (MRI), high frequency ultrasound (HFU), positron emission tomography (PET), optical coherence tomography (OCT), intra-vascular ultrasound (IVUS), ultrasound, intra-operative CT or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sites within the patient 14. It should further be noted that the imaging device 12, as shown in FIG. 1, provides a virtual bi-plane image using a single-head C-arm fluoroscope as the imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, introduced and advanced in the patient 14, may be superimposed in more than one view on display 36 allowing simulated bi-plane or even multi-plane views, including two and three-dimensional views, as will be discussed in greater detail herein.

With continuing reference to FIG. 1, if the navigation system 10 is an electromagnetic (EM) system, the navigation system 10 can further include an EM navigation or tracking system 44 that includes a localizer, such as a transmitter coil array 46, the coil array controller 48, a navigation probe interface 50, and instruments 52, such as an instrument 52a for use in the image guided procedure and a dynamic reference frame or DRF 52b.

The instrument 52a may be any appropriate instrument, such as an instrument for preparing a portion of the patient or positioning an implant. The transmitter coil array 46 may also be supplemented or replaced with a mobile localizer 46a. The mobile localizer 46a may be one such as that described in U.S. patent application Ser. No. 10/941,782, filed Sep. 15, 2004, and entitled "METHOD AND APPARATUS FOR SURGICAL NAVIGATION", herein incorporated by reference.

Further included in the navigation system 10 may be an isolator circuit or box 55. The isolator circuit or box 55 may be included in a transmission line to interrupt a line carrying a signal or a voltage to the navigation probe interface 50. Alternatively, the isolator circuit included in the isolator box 55 may be included in the navigation probe interface 50, the instrument 52a, the DFR 52b, the transmission lines coupling the devices, or any other appropriate location. The isolator box 55 is operable to isolate any of the instruments or patient coincidence instruments or portions that are in contact with the patient should an undesirable electrical surge or voltage take place.

In addition, the navigation system 10 can further include a gating device or an ECG or electrocardiogram (not shown), which is attached to the patient 14, via skin electrodes, and in communication with the coil array controller 48. Respiration and cardiac motion can cause movement of cardiac structures relative to the instrument 52, even when the instrument 52 has not been moved. Therefore, images can be acquired from the imaging system 12 based on a time-gated basis triggered by a physiological signal. For example, the ECG or EGM signal may be acquired from the skin electrodes or from a sensing electrode included on the instrument 52 or from a separate reference probe (not shown). A characteristic of this signal, such as an R-wave peak or P-wave peak associated with ventricular or atrial depolarization, respectively, may be used as a triggering event for the coil array controller 48 to drive the coils in the transmitter coil array 46. This triggering event may also be used to gate or trigger image acquisition during the imaging phase with the imaging device 12. By time-gating the image data and/or the navigation data, the icon of the location of the instrument 52 in image space relative to the patient space 14 at the same point in the cardiac cycle may be displayed on the display 36.

It should further be noted that the entire EM tracking system 44 or parts of the EM tracking system 44 may be incorporated into the imaging device 12, including the workstation 34 and radiation sensors 24. Incorporating the EM tracking system 44 may provide an integrated imaging and tracking system. Any combination of these components may also be incorporated into the imaging device 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. The transmitter coil array 46 may also be positioned in the items being navigated. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in a tracking sensor 58 positioned on or in the instrument 52. These induced signals from the instrument 52 are delivered to the navigation probe interface 50 through the isolator box 55 and subsequently forwarded to the coil array controller 48. The navigation probe interface 50 may provide all the necessary electrical isolation for the navigation system 10. The navigation probe interface 50 can also include amplifiers, filters and buffers to directly interface with the tracking sensors 58 in the instrument 52. Alternatively, the instrument 52 may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the instrument 52a, the DRF 52b, the probe 66, and others as will be described in detail below, are equipped with at least one, and generally multiple, tracking sensors 58, that may also be referred to as localization sensors. The instrument 52a can be a handle or inserter that interconnects with an attachment and may assist in placing an implant or in driving a portion. The instrument 52a can include a graspable or manipulable portion at a proximal end and the tracking sensor 58 may be fixed near the manipulable portion of the instrument 52a. The tracking sensor 58 can include an electromagnetic sensor such that the electromagnetic field generated by the transmitter coil array 46 may induce a current in the tracking sensor 58.

In an alternate embodiment, the electromagnetic sources or generators may be located within the instrument 52a, DRF 52b, probe 66 and one or more receiver coils may be provided externally to the patient 14 forming a receiver coil array similar to the transmitter coil array 46. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

The DRF 52b of the tracking system 44 is also coupled to the navigation probe interface 50 to forward the information to the coil array controller 48. The DRF 52b, according to various embodiments, may include a small magnetic field detector. The DRF 52b may be fixed to the patient 14 adjacent to the region being navigated so that any movement of the patient 14 is detected as relative motion between the transmitter coil array 46 and the DRF 52b. This relative motion is forwarded to the coil array controller 48, which updates registration correlation and maintains accurate navigation, further discussed herein. The DRF 52b may include any appropriate tracking sensor used by the navigation system 10. Therefore the DRF 52b may also be optical, acoustic, etc. If the DRF 52b is electromagnetic it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the radiological image generated from the imaging device 12 and the corresponding points in the patient's anatomy in patient space. After this map is established, whenever a tracked instrument, such as the instrument 52a or a pointing device or probe 66 is used, the workstation 34 in combination with the coil array controller 48 and the controller 28 uses the translation map to identify the corresponding point on the pre-acquired image or atlas model, which is displayed on display 36. This identification is known as navigation or localization. An icon representing the localized point or instruments is shown on the user interface 38 within several two-dimensional image planes, as well as on three and four dimensional images and models, as will be discussed herein.

To enable navigation, the navigation system 10 must be able to detect both the position of the patient's anatomy and the position of the instrument 52a or attachment member attached to the instrument 52a. Knowing the location of these two items allows the navigation system 10 to compute and display the position of the instrument 52a in relation to the patient 14. The tracking system 44 is employed to track the instrument 52a and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the tracking system 44 can determine the position of the instrument 52a by measuring the field strength at the tracking sensor 58 location. The DRF 52b is fixed to the patient 14 to identify the location of the patient in the navigation field. The tracking system 44 continuously recomputes the relative position of the DRF 52b and the instrument 52a during localization and relates this spatial information to patient registration data to enable image guidance of the instrument 52a within and/or relative to the patient 14.

Patient registration is the process of determining how to correlate the position of the instrument 52a relative to the patient 14 to the position on the diagnostic or pre-acquired images. To register the patient 14, a physician or user 67 may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space, as discussed herein. The points that are selected to perform registration are the fiducial markers or markers 60, such as anatomical landmarks. Again, the landmarks or fiducial markers 60 are identifiable on the images and identifiable and accessible on the patient 14. The markers 60 can be artificial markers 60 that are positioned on the patient 14 or anatomical landmarks that can be easily identified in the image data. The artificial landmarks, such as the fiducial markers 60, can also form part of the DRF 52b, such as those disclosed in U.S. Pat. No. 6,381,485, entitled "Registration of Human Anatomy Integrated for Electromagnetic Localization," issued Apr. 30, 2002, herein incorporated by reference.

The navigation system 10 may also perform registration using anatomic surface information or path information as is known in the art. The navigation system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 60/465,615, entitled "Method and Apparatus for Performing 2D to 3D Registration" filed on Apr. 25, 2003, hereby incorporated by reference.

The navigation system 10 can be used according to any appropriate method or system. For example, pre-acquired images, atlas or 3D models may be registered relative to the patient and patient space. Generally, the navigation system 10 allows the images on the user interface 38 to be registered and to accurately display the real time location of the various instruments, such as the instrument 52a, and other appropriate items, such as the pointer probe 66. In addition, the pointer probe 66 may be used to register the patient space to the pre-acquired images or the atlas or 3D models. In addition, the DRF 52b may be used to ensure that any planned or unplanned movement of the patient or the transmitter coil array 46 is determined and used to correct the image on the display 36.

It will be understood that the tracking system employed with the navigation system 10 may also be any appropriate tracking system, such as an optical tracking system 44a. Further, other tracking systems could be employed by the navigation system 10, such as an acoustic, radiation, etc. However, if the optical tracking system 44a is used, the optical tracking system 44a can include a camera 47 and either passive or reflective tracking devices that can be attached to the instruments 52. The camera 47 can be an optical localizer such as used in the StealthStation® TRIA™ sold by Medtronic Navigation of Louisville, Colo. The optical tracking system 44a is generally considered a line of sight tracking system as the instruments 52 are tracked based on their optical visibility to the camera 47. Thus, the instrument 52a and DRF 52b can include active or passive optical tracking sensors, such as the optical tracking sensor 58a. An active optical tracking sensor 58a can include at least one light emitting feature, such as an infrared light emitting diode, that can be recognized by the camera 47. A passive optical tracking sensor 58a can include at least one reflector to reflect an optical beam generated by the camera 47.

Figure 2:
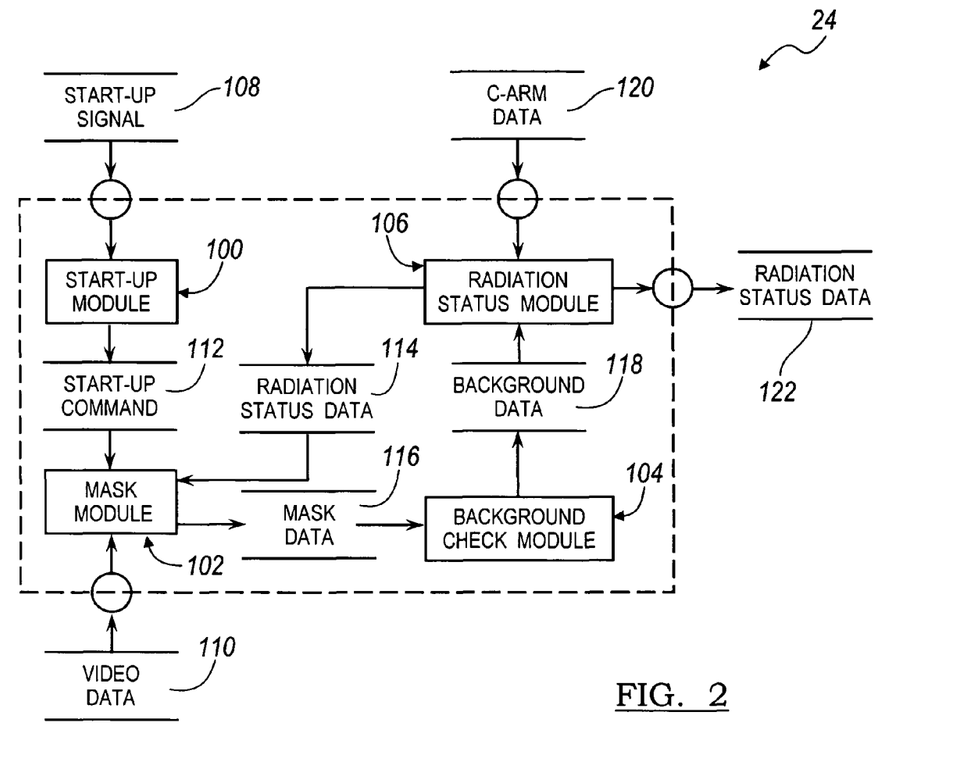
FIG. 2 is a dataflow diagram illustrating an exemplary radiation status control system performed by a radiation status control module.

As discussed above, the radiation status control module 24 detects the status of the x-ray source 18, and thus, identifies if the x-ray source 18 is actively imaging. The radiation status control module 24 then outputs this information to the C-arm controller 28. With reference to FIG. 2, a dataflow diagram illustrates various components of a radiation status control system that can be embedded within the control module 24. Various embodiments of the radiation status control system according to the present disclosure can include any number of sub-modules embedded within the control module 24. The sub-modules shown may be combined and/or further partitioned to similarly determine the acquisition of a fluoroscopic image by the x-ray source 18. Inputs to the system can be received from the receiving section 20 and the C-arm controller 28 of the imaging device 12, or even received from other control modules (not shown) within the navigation system 10, and/or determined by other sub-modules (not shown) within the control module 24 (not shown). In various embodiments, the control module 24 includes a start-up module 100, a mask module 102, a background check module 104, and a radiation status module 106.

The start-up module 100 can receive as input a start-up signal 108. The start-up signal 108 can indicate an initialization of the x-ray source 18. The start-up module 100 can enable communication between the receiving section 20 of the imaging device 12 and the control module 24. Establishing communication between the imaging device 12 and the control module 24 can enable the control module 24 to receive as input video data 110 from the receiving section 20. Generally, the start-up module 100 can set a start-up command 112 to the mask module 102. The mask module 102 can receive as input the start-up command 112, the video data 110 and radiation status data 114. The video data 110 can comprise a series of fluoroscopic images in a bitmap format, for example. The mask module 102 can examine the video data 110 to create a mask for each image in the video data 110. Generally, the mask module 102 can create the mask based on the radiation status data 114. The radiation status data 114 can indicate the status of the x-ray source 18. As will be discussed herein, the radiation status data 114 can generally comprise an ON indication, an OFF indication and an UNKNOWN indication associated with whether the x-ray source 18 is active. If a mask is created, the mask module 102 can set mask data 116 for the background check module 104, as will be discussed herein.

The background check module 104 can receive as input the mask data 116 from the mask module 102. Based on the mask data 116, the background check module 104 can set background data 118 for the radiation status module 106. The background data 118 can comprise data regarding the content of a background area defined by the mask data 116. The radiation status module 106 can receive as input the background data 118 and C-arm data 120. The C-arm data 120 can indicate the type of C-arm 16 used to take the fluoroscopic image. Based on the background data 118 and C-arm data 120, the radiation status module 106 can set radiation status data 114 for the mask module 102 and output radiation status data 122 for the C-arm controller 28. The radiation status data 114, 122 can comprise the ON indication, the OFF indication, and the UNKNOWN indication associated with whether the x-ray source 18 is actively imaging.

Figure 3:
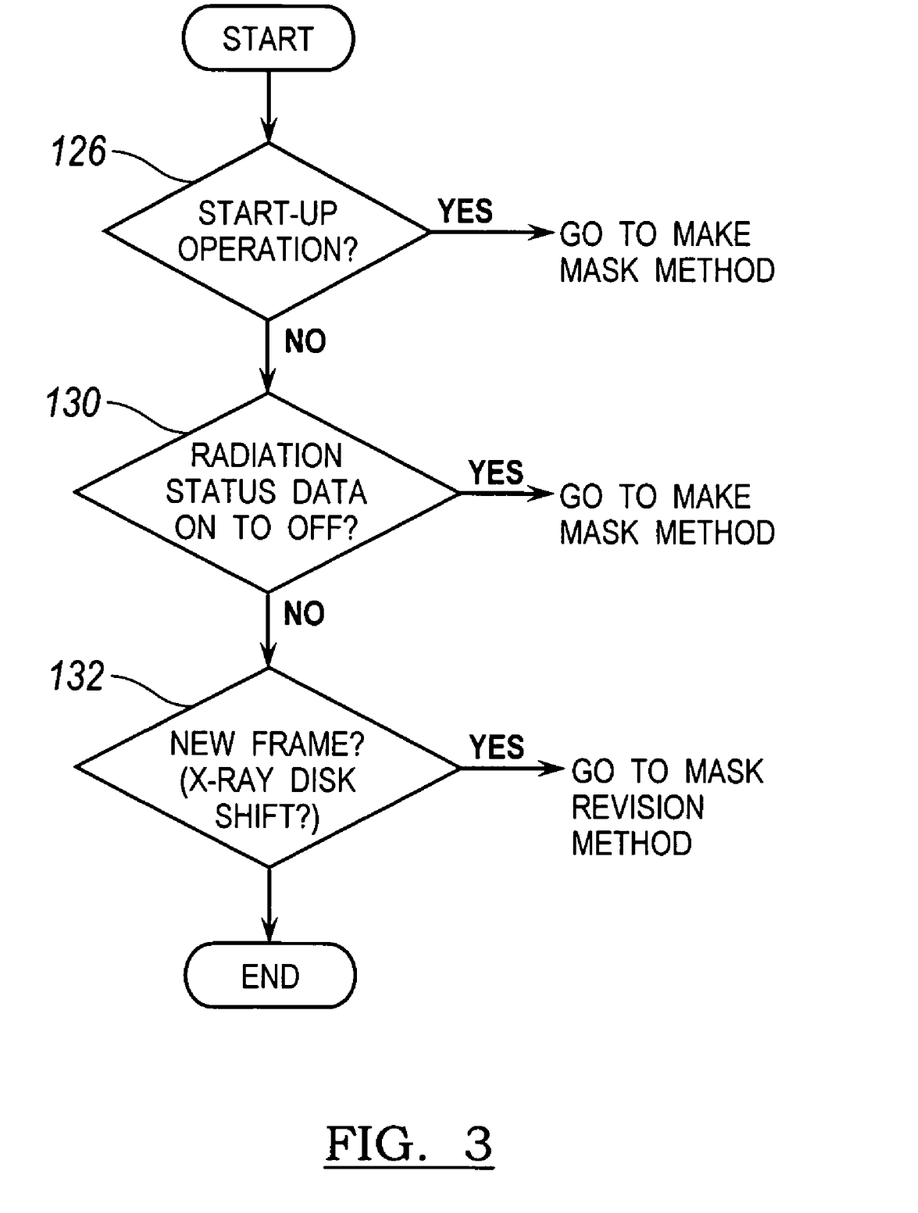
FIG. 3 is a flowchart illustrating an initial method performed by a mask module of the radiation status control module.
Figure 5:
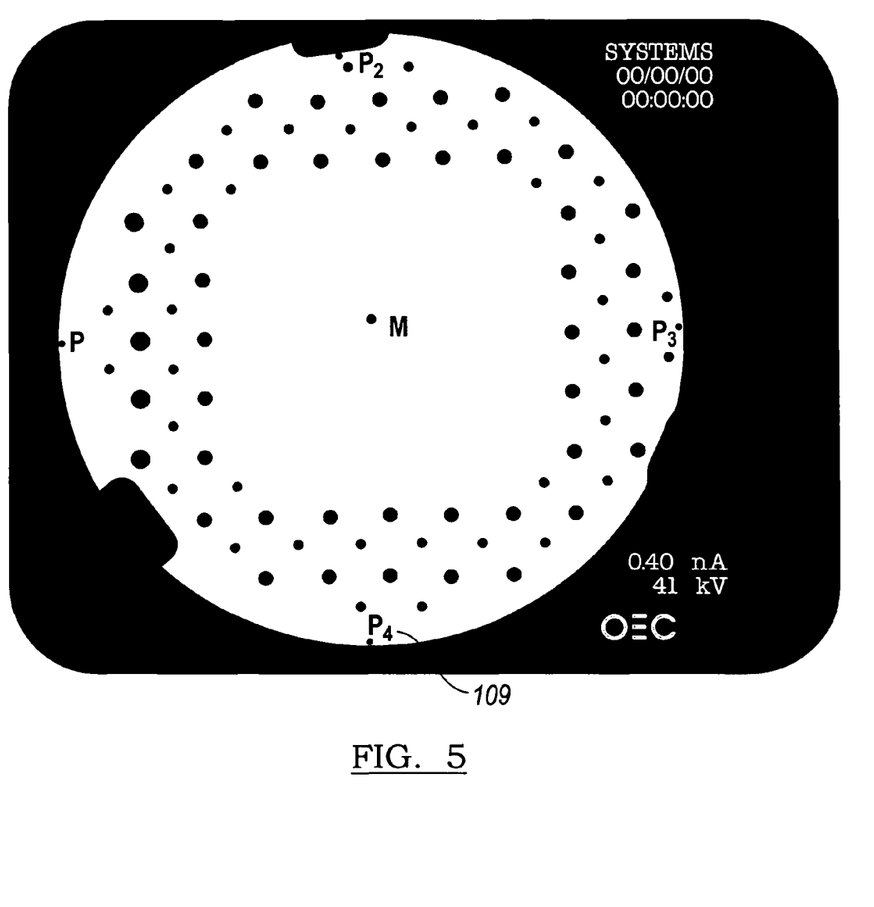
FIG. 5 is an exemplary fluoroscopic image illustrating a radiation OFF event.

Referring now to FIG. 3, a flowchart illustrates an initial method performed by the mask module 102. At 126, control determines if the mask module 102 just received the start-up command 112, such that the control module 24 is creating a mask in response to a start-up operation. If the mask module 102 was initiated by the start-up command 112, then control proceeds to the make mask method. If the mask module 102 was not initiated in a start-up operation, then control determines, based on the radiation status data 114, if the radiation status has changed from an ON indicator to an OFF indicator at 130. If the radiation status has changed from the ON indicator to the OFF indicator, then control goes to the make mask method. If the radiation status data 114 does not indicate a change from the ON indicator to the OFF indicator, then control goes to 132. At 132, control determines if the video data 110 received by the mask module 102 is associated with a new frame. Each new frame can be checked against the last frame to determine if a shift of an x-ray disk 109 in the fluoroscopic image has occurred (FIG. 5). If the video data 110 is associated with a new frame, then control goes to the revise mask method.

Figure 4:
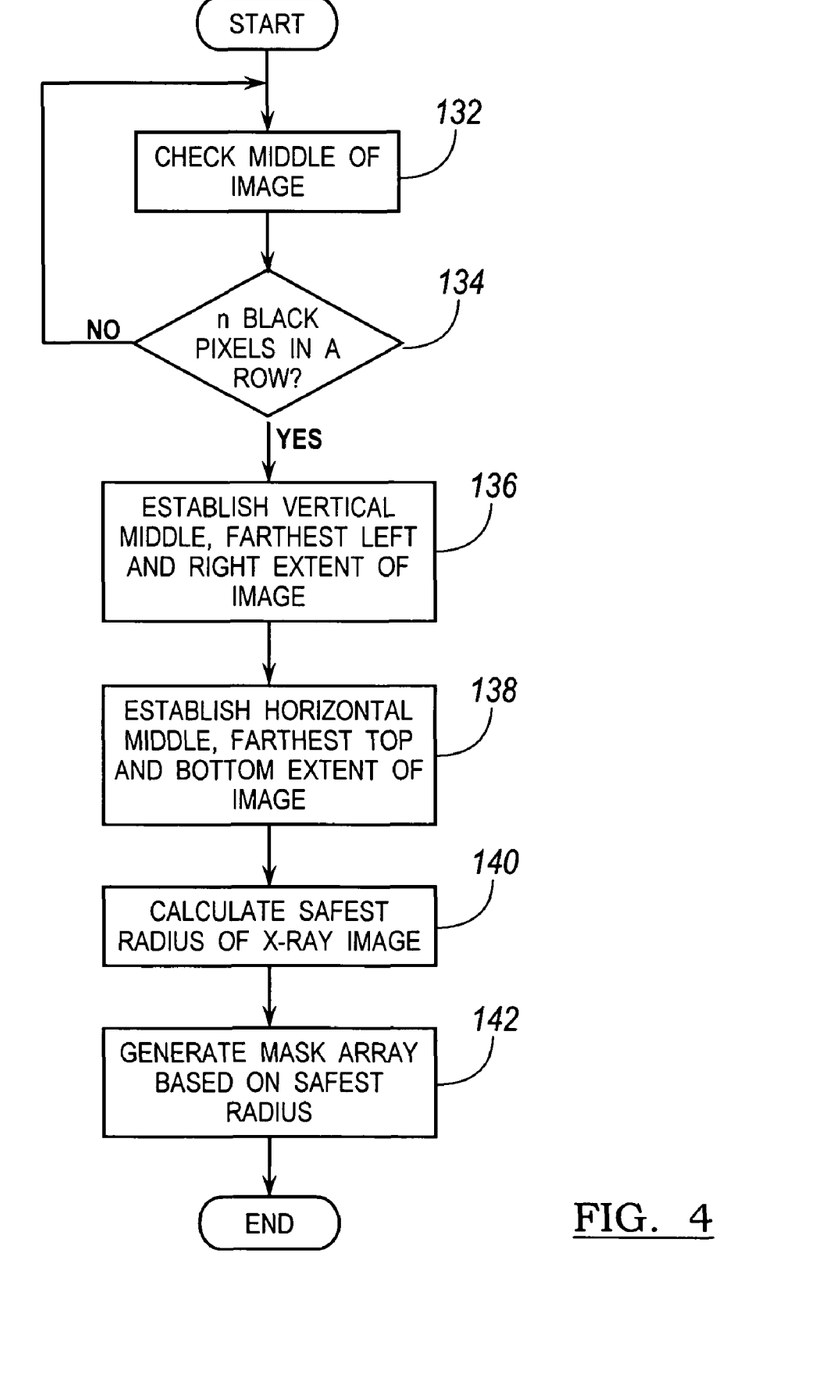
FIG. 4 is a flowchart illustrating a method performed by the mask module of the radiation status control module.

With reference now to FIG. 4, a flowchart illustrates the make mask method performed by the mask module 102. A mask is necessary to filter out the x-ray disk 109 from the video data 110, as will be discussed in greater detail herein. Generally, the mask is created as an array of integers that are paired values representing the starting and ending address of each line in the background of the fluoroscopic image, with the background of the fluoroscopic image being associated with the remainder of the fluoroscopic image after the x-ray disk 109 has been removed from the fluoroscopic image. At 132 control can check for a middle M of the fluoroscopic image, as shown in FIG. 5. From the middle M of the fluoroscopic image, control at 134 can determine if there are n number of black pixels in a row. Generally, control can examine a predefined number of rows of the fluoroscopic image until locating a point P where there are n number of black pixels in a row.

For example, control could check every 20 rows from the middle M of the fluoroscopic image to the outside of the fluoroscopic image looking for the point P where there are 15 black pixels in a row. It should be noted that depending upon the desired accuracy of the mask module 102, the number of rows examined and the number of n pixels used could range, such as from examining every row to every $35^{th}$ row for five to 25 black pixels in a row. Generally, the number of rows examined and number of pixels can depend upon the smudges and target ball shadowing associated with the particular x-ray disk 109 created by the particular C-arm 16 employed.

Once control finds n number of black pixels in a row, control at 136 establishes the vertical middle M, the farthest left point P and farthest right point $P_3$ of the x-ray disk 109 in the fluoroscopic image (FIG. 5). At 138, control establishes the horizontal middle M, farthest top point $P_2$ and farthest bottom point $P_4$ associated with the x-ray disk 109 in the fluoroscopic image. Generally, control can establish the horizontal middle M, farthest top point $P_2$ and farthest bottom point $P_4$ by examining a predefined number of columns in the fluoroscopic image for n black pixels in a row. For example, control can examine every 20 columns for the point $P_2$ in which there are 15 black pixels in a row (FIG. 5). As discussed, the number of columns and the number of black pixels evaluated by control can be based on the desired accuracy of the mask module 102, and can range from examining every column to every $35^{th}$ column for five to 25 black pixels in a row. Generally, the number of columns examined and number of pixels can depend upon the smudges and target ball shadowing associated with the particular x-ray disk 109 created by the particular C-arm 16 employed.

Once the vertical middle, horizontal middle, farthest left point, farthest right point, farthest top point and farthest bottom point are determined, control can calculate a radius of the x-ray disk 109 in the fluoroscopic image at 140. Once the radius is calculated, control determines if the radius is "safe." A "safe" radius is one that is not larger than half of the image width or smaller than a third of the image height. If the image is "safe", then at 142, control can generate the mask array based on the "safe" radius. Generally, each address in the mask array can be associated with a black pixel. In this regard, the starting point is the address of a black pixel on the radius, and the ending point is a black pixel associated with the edge of the fluoroscopic image. Typically, in an exemplary mask array, the first entry can be zero and the last entry can be the image width multiplied by the height minus one. The entries in between the first and the last image are that of the addresses of the black pixels associated with the edge of the x-ray disk 109 in the fluoroscopic image as determined by the "safe" radius. Generally, there can be up to two times the number of rows in the fluoroscopic image plus two members in the mask array.

Figure 6:
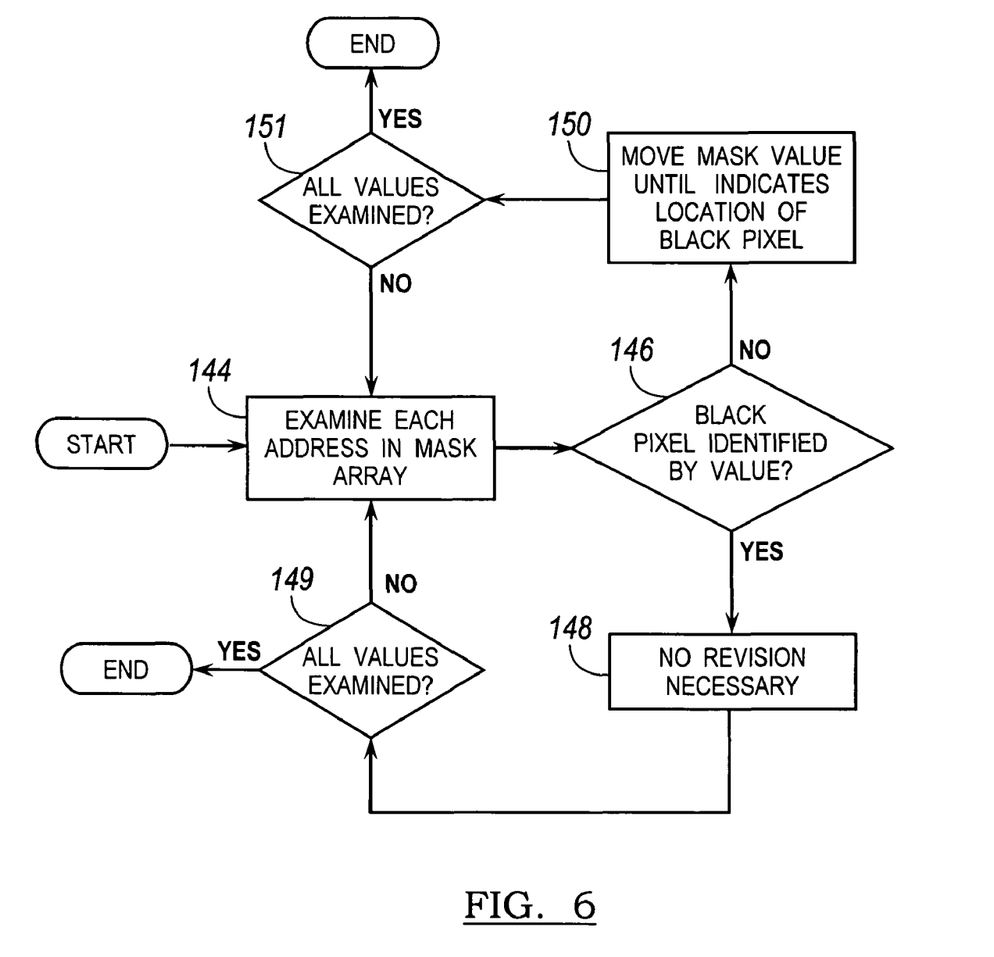
FIG. 6 is a flowchart illustrating a mask revision method performed by the mask module of the radiation status control module.

With reference now to FIG. 6, a flowchart illustrates the mask revision method performed by the mask module 102 to determine if the x-ray disk 109 has shifted on the fluoroscopic image. At 144, control examines an address in the mask array. If a black pixel is identified by the address at 146, then at 148 control determines that no revision is necessary. Then, control at 149 determines if each address in the mask array has been examined. If each address in the mask array has not been examined, then control loops to 144. Otherwise, the mask revision method ends.

If during the examination of the address in the mask array at 146, a black pixel is not identified by the address, then control increments the address until it identifies a black pixel at 150. For example, if control is examining a value in an address that represents the left side of the mask, such as an even numbered array entry, then control can move that value in the address left (positive direction). If, however, control is examining a value in an address that represents the right side of the mask, such as an odd numbered array entry, then the value in the address can be moved right (negative direction).

After the address has been moved to represent a black pixel, control can determine at 150 if all of the addresses in the mask array have been examined. If there are addresses remaining to be examined, then control can loop to 144. If, however, all the mask addresses are examined, then control ends the revise mask method. It should be noted that the number of moves required to adjust the addresses in the mask array can be associated with a quality of the mask array. If desired, a threshold can be implemented in which if the amount of moves required to revise the mask exceeds a predefined threshold, then a new mask can be created.

Figure 7:
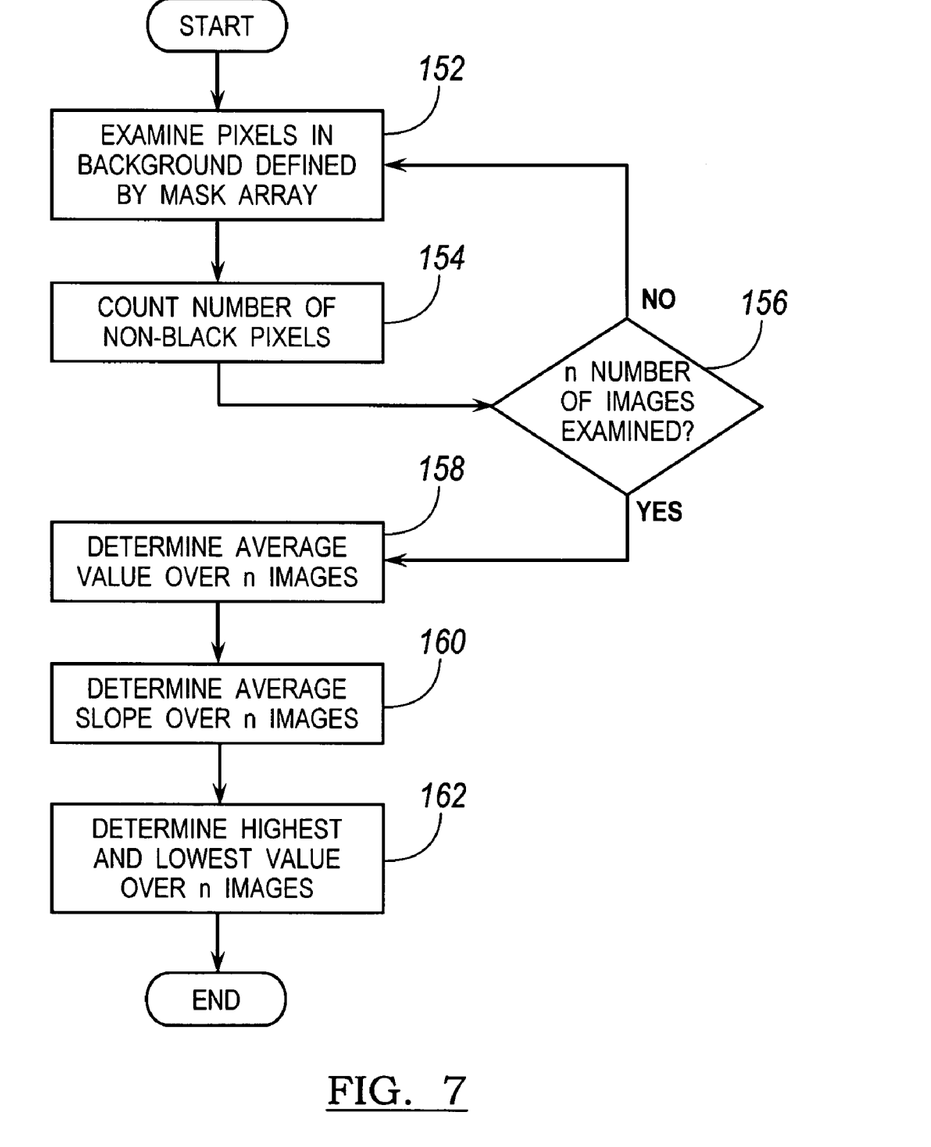
FIG. 7 is a flowchart illustrating a background check method performed by a background check module of the radiation status control module.

Referring now to FIG. 7, a flowchart illustrates a method performed by the background check module 104. At 152, control can examine a predefined number of pixels in the background of the fluoroscopic image as defined by the mask array. For example, control can examine every other pixel in each background line defined by the address in the mask array, but, if desired, control could examine every pixel or every third pixel. Then, at 154, control can count the number of non-black pixels in the examined background line. At 156, control can determine if it has examined a predefined n number of fluoroscopic images. If control has not examined the defined number of fluoroscopic images, then control loops to 152 until control has examined the appropriate number of images. For example, the appropriate number of fluoroscopic images can be six, but can range from two to ten depending on the noise reduction necessary and speed desired for the background check module 104.

After the desired number of fluoroscopic images has been examined by the background check module 104, at 158, control can determine the average value of the non-black pixels over n fluoroscopic images. Then, at 160, control can determine the average slope of the non-black pixels over n fluoroscopic images. At 162, control can determine the highest and lowest value of the non-black pixels over the n fluoroscopic images. The average value, average slope, highest and lowest values of the non-black pixels can then be set as background data 118 for the radiation status module 106.

Figure 8:
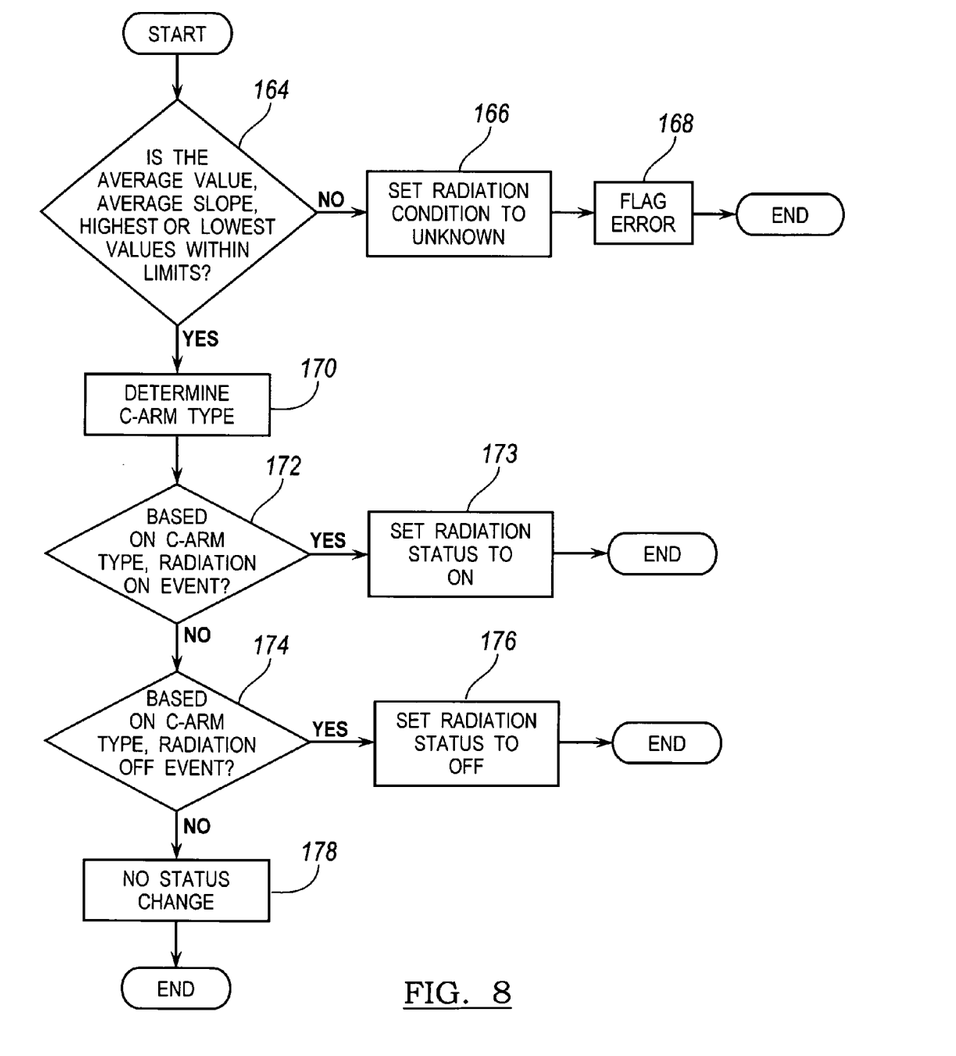
FIG. 8 is a flowchart illustrating a radiation status method performed by a radiation status module of the radiation status control module.

With reference now to FIG. 8, a flowchart illustrates a radiation status method that can be performed by the radiation status module 106. At 164, control can determine if the average value, average slope, highest and lowest values of the non-black pixels are within predefined limits. The predefined limits are associated with the noise of the stream of video data 110. If the noise in the video data 110 stream exceeds the predefined limits, then at 166 control can set the radiation status to "UNKNOWN" and flag an error at 168. Then the method can go to 130.

If the average value, average slope, highest and lowest values of the non-black pixels are within predefined limits, then at 170, control can determine the type of C-arm 16 used to take the fluoroscopic images. Exemplary C-arms that could be employed to take the fluoroscopic images are: The GE OEC® 9800 and GE OEC® 9600, manufactured by GE Heathcare of Chalfont St. Giles, United Kingdom, the Pulsara, manufactured by Royal Philips Electronics of Amsterdam, Netherlands and the Orbic Iso-C, manufactured by Siemens AG of Munich, Germany. The type of C-arm 16 used to take the fluoroscopic images is required as each C-arm 16 has a characteristic signature associated with a radiation ON and radiation OFF event, as will be discussed herein.

At 172, based on the type of C-arm 16, control can determine if a radiation ON event has occurred. If a radiation ON event has occurred, then control can set the radiation status data 114, 122 to ON at 173. In order to determine if a radiation ON event has occurred, control can compare the background data 118 received from the background check module 104 to the known signature ON event associated with the particular C-arm 16. With reference to Table 1, an exemplary signature ON event for each C-arm 16 is listed including any conditions associated with identifying the radiation ON event.

TABLE 1

Radiation ON Event Signatures for Exemplary C-Arms

| Model | Radiation ON Event Signature | Report ON Event If |
|---|---|---|
| GE OEC® 9600 | Examine images for a low dip in the number of non-black pixels in the background (identifies a blanking of the background) | Low dip in the number of non-black pixels is sustained longer than half a second |
| PHILIPS | Examines images for a low dip in the number of non-black pixels from a starting value of non-black pixels, and then a partial return to the starting value of non-black pixels | Overly high values of non-black pixels are factored out (so that a subsequent return to a low value of non-black pixels does not trigger an ON event) |
| SIEMENS | Examine images for a low dip in the number of non-black pixels in the background for a brief period of time (identifies a blanking of the background), followed by a significant return in the number of non-black pixels | Determining the blanking of the background provides a true radiation ON event, even in the case of when the background text is not on |

Thus, for a GE OEC® 9600 model C-arm 16, the radiation ON event is identified by a low dip in the number of non-black pixels in the background of the fluoroscopic image, so long as the low dip in the number of non-black pixels is sustained longer than half a second.

With reference back to FIG. 8, if a radiation ON event has not been determined by control, then at 174 control can determine if a radiation OFF event has occurred based on the type of C-arm 16 employed. If a radiation OFF event has occurred, then at 176, control can set the radiation status data 114, 122 to OFF. In order to determine if a radiation OFF event has occurred, control can compare the background data 118 received from the background check module 104 to the known signature OFF event associated with the particular C-arm 16. With reference to Table 2, an exemplary signature OFF event for each C-arm 16 is listed.

TABLE 2

Radiation OFF Event Signatures for Exemplary C-Arms

| Model | Radiation OFF Event Signature |
|---|---|
| GE OEC ® 9600 | Examine images for a partial return to the starting value of non-black pixels followed by a low dip in the number of non-black pixels and then a return to the starting value of non-black pixels in the background (associated with a return of text in the background) |
| PHILIPS | Examines images for a return to a starting value of non-black pixels that is associated with a total return of text in the background |
| SIEMENS | If text is left on, radiation OFF event can be identified by the an increase in the number of non-black pixels indicating a return of an ID text string in the background; if text is turned off, then radiation OFF event identified by an increase in the number of non-black pixels indicating a return of the background text |

Thus, for a GE OEC® 9600 model C-arm, the radiation OFF event is identified by a partial return to the starting value of the number of non-black pixels in the background followed by a low dip in the number of non-black pixels and then a return to the starting value of the non-black pixels in the background, as shown in FIG. 5.

With reference back to FIG. 8, if a radiation OFF event has not occurred as determined by control at 174, then, at 178, control can indicate that there has been no change in the status of the radiation.

Thus, in order to determine if the imaging device 12 is actively imaging, after the start-up module 100 has established communication between the imaging device 12 and the control module 24 to enable the control module 24 to receive the video data 110, the mask module 102 can perform the make mask method to establish a mask for the given video data 110 stream. Based on the mask data 116 (mask array) created by the make mask method, the background check module 104 can examine the background of the fluoroscopic image to determine the parameters of the non-black pixels in the background of the fluoroscopic image.

Given the particular parameters of the non-black pixels over a given stream of video data 110, control can determine, using the radiation status module 106, a status of the imaging device 12, such as whether the imaging device 12 is actively imaging. In particular, control can determine based on the type of C-arm 16 and the parameters of the non-black pixels over the video data 110 stream if the C-arm 16 is experiencing a radiation ON event, a radiation OFF event or an UNKNOWN radiation event. The indication of a radiation ON event, radiation OFF event or UNKNOWN radiation event can then be outputted to the C-arm controller 28.

By determining when the C-arm 16 is active, the computer 34 can properly determine if the image later acquired from the imaging device 12 is an updated image so that the computer 34 can correlate the current location of the surgical devices with regard to the current location of the patient 14. Thus, in case the patient 14 and/or instrument 52 has moved since the last acquired fluoroscopic image, the detection of a radiation ON event to a radiation OFF event, or vice versa, can signal the computer 34 to re-correlate the location of the instrument 52 and the patient 14 with the prior established location of the instrument 52 and/or patient 14, such that any change in the location of the instrument 52 and/or patient 14 is updated in the patient space. This correlation of the newly acquired fluoroscopic images to the locations established by the prior acquired fluoroscopic images (pre-operative and/or intra-operative) can enhance the accuracy of the navigation system 10.

The description of the teachings herein is merely exemplary in nature and, thus, variations that do not depart from the gist of the teachings are intended to be within the scope of the teachings. Such variations are not to be regarded as a departure from the spirit and scope of the teachings.

What is claimed is:

1. A system for detecting a status of an imaging device for use with a surgical navigation system comprising:
   a source of at least one image;
   a mask module that generates a mask array for each received image;
   a background check module that determines a content of non-black pixels in the image defined by the mask array;
   a radiation status module that determines a status of the imaging device based on the content of the non-black pixels in the image; and
   wherein the status of the imaging device is ON, OFF or UNKNOWN.

2. The system of claim 1, further comprising:
   a start-up module that enables communication between the source of at least one image and the mask module upon receipt of a start-up signal.

3. A system for detecting a status of an imaging device for use with a surgical navigation system comprising:
   a source of at least one image;
   a mask module that generates a mask array for each received image;
   a background check module that determines a content of the image defined by the mask array;
   a radiation status module that determines a status of the imaging device based on the content of the image; and
   wherein the mask module determines a middle of the image and then examines the image from the middle for an n number of black pixels in a row.

4. The system of claim 3, wherein n ranges between 10 to 20 pixels.

5. A system for detecting a status of an imaging device for use with a surgical navigation system comprising:
   a source of at least one image;
   a mask module that generates a mask array for each received image;
   a background check module that determines a content of the image defined by the mask array;
   a radiation status module that determines a status of the imaging device based on the content of the image;

wherein the mask module determines the vertical middle, horizontal middle, the farthest top point, farthest bottom point, farthest left point and farthest right point of the image; and wherein the mask module computes a radius of the mask based on the vertical middle, horizontal middle, the farthest top point, farthest bottom point, farthest left point and farthest right point of the image and generates the mask array to consist of addresses of background lines existing outside of a circle defined by the computed radius.

6. The system of claim 5, wherein the image is a fluoroscopic image and the circle defined by the mask module is equivalent to an x-ray disk defined in the fluoroscopic image.

7. The system of claim 6, wherein the mask module examines each mask array value of the fluoroscopic image if the mask module determines a shift in the x-ray disk defined in the fluoroscopic image.

8. The system of claim 7, wherein the mask module moves each mask array value until the array value indicates an address of a black pixel if the examined mask array value is not the address of a black pixel.

9. A system for detecting a status of an imaging device for use with a surgical navigation system comprising:
   a source of at least one image;
   a mask module that generates a mask array for each received image;
   a background check module that determines a content of the image defined by the mask array;
   a radiation status module that determines a status of the imaging device based on the content of the image; and
   wherein the background check module computes the number of non-black pixels in a background defined by an area of the image outside of the mask array.

10. The system of claim 9, wherein the background check module determines the average value of the non-black pixels, the average slope of the non-black pixels, the highest value of the non-black pixels and the lowest value of the non-black pixels over a series of n images.

11. The system of claim 10, wherein n ranges from 3 to 10 images.

12. The system of claim 10, wherein the radiation status module sets the radiation status to UNKNOWN if at least one of the average value of the non-black pixels, the average slope of the non-black pixels, the highest value of the non-black pixels and the lowest value of the non-black pixels over the series of n images is outside of predefined limits.

13. The system of claim 10, wherein the radiation status module determines the radiation status as ON or OFF based on a type of imaging device used and at least one of the average value of the non-black pixels, the average slope of the non-black pixels, the highest value of the non-black pixels and the lowest value of the non-black pixels over the series of n images.

14. The system of claim 1, further comprising:
   a navigation system that navigates a tracking device relative to an anatomy using the imaging device.

15. The system of claim 14, wherein the imaging device is selected from the group comprising an isocentric fluoroscopy device, a bi-plane fluoroscopy device, an ultrasound device, a computed tomography (CT) device, a multi-slice computed tomography (MSCT) device, a magnetic resonance imaging (MRI) device, a high frequency ultrasound (HFU) device, a positron emission tomography (PET) device, an optical coherence tomography (OCT) device, an intra-vascular ultrasound (IVUS) device, an intra-operative CT device, an intra-operative MRI device and combinations thereof.

16. A method of detecting a status of an imaging device for use with a surgical navigation system comprising:
   providing a source of at least one image;
   generating a mask for the image, the mask defining a background area of the at least one image;
   determining a content of non-black pixels in the background area of the at least one image; and
   determining, based on the content of the non-black pixels in the background area of the at least one image, if the imaging device is ON.

17. The method of claim 16, wherein providing a source of at least one image further comprises:
   providing a source of at least one fluoroscopic image.

18. A method of detecting a status of an imaging device for use with a surgical navigation system comprising:
   providing a source of at least one fluoroscopic image;
   generating a mask for the at least one fluoroscopic image, the mask defining a background area of the at least one fluoroscopic image;
   determining a content of the background area of the at least one fluoroscopic image;
   determining, based on the background area of the at least one fluoroscopic image, a status of the imaging device; and
   wherein determining the mask for the at least one fluoroscopic image further includes:
      locating the middle of the at least one fluoroscopic image;
      examining the at least one fluoroscopic image from the middle of the at least one fluoroscopic image for a pre-defined number of black pixels in a row; and
      generating the mask as an array of addresses associated with the at least one fluoroscopic image, the array of addresses corresponding to a plurality of black pixels that form a circumference of an x-ray disk defined in the at least one fluoroscopic image.

19. The method of claim 18, wherein generating the mask as the array of addresses further comprises:
   generating a first integer equivalent to a starting address of a line of pixels in the background area of the at least one fluoroscopic image; and
   generating a second integer equivalent to an ending address of the line of pixels in the background area.

20. The method of claim 18, wherein generating the array corresponding to a circumference of the at least one fluoroscopic image further comprises:
   determining a vertical middle of the at least one fluoroscopic image;
   determining a farthest left point of the at least one fluoroscopic image;
   determining a farthest right point of the at least one fluoroscopic image;
   determining a horizontal middle of the at least one fluoroscopic image;
   determining a farthest top point of the at least one fluoroscopic image;
   determining a farthest bottom point of the at least one fluoroscopic image; and
   generating the circumference of the at least one fluoroscopic image based on the vertical middle, farthest left point, farthest right point, horizontal middle, farthest top point and farthest bottom point of the at least one fluoroscopic image.

21. The method of claim 18, further comprising:
   revising the array if a shift in the circumference of the x-ray disk defined in the at least one fluoroscopic image is observed.

22. The method of claim 21, further comprising:
    determining if each address in the array is still associated with the location of a black pixel on the circumference of the at least one fluoroscopic image; and
    shifting the address to a black pixel if the address identifies a non-black pixel.

23. A method of detecting a status of an imaging device for use with a surgical navigation system comprising:
    providing a source of at least one image;
    generating a mask for the image, the mask defining a background area of the image;
    determining a content of the background area of the image;
    determining, based on the background area of the image, a status of the imaging device;
    computing the number of non-black pixels in the background defined by the mask;
    determining, based on a series of images, an average value, an average slope, a highest value and a lowest value of non-black pixels in the background area of the image;
    determining a type of imaging device employed with the type of imaging device denoting a signature related to the content of non-black pixels in an image during active imaging; and
    determining if the imaging device is active based on a comparison between the signature associated with the type of imaging device and the average value, the average slope, the highest value and the lowest value of non-black pixels in the background area of the image.

24. A method of tracking a portion of an anatomy comprising:
    providing an imaging device;
    coupling a tracking device to at least one of the anatomy or an instrument;
    tracking the tracking device relative to the anatomy;
    generating at least one image;
    generating a mask for the image, the mask defining a background of the image;
    detecting a content of non-black pixels in a background of the image; and
    determining a status of the imaging device based on the content of non-black pixels in the background and the imaging device used.

25. The method of claim 24, further comprising:
    providing a fluoroscopic imaging device; and
    generating at least one fluoroscopic image.

26. The method of claim 25, wherein generating the mask for the image further comprises:
    locating the middle of the fluoroscopic image;
    examining the fluoroscopic image from the middle of the fluoroscopic image for a pre-defined number of black pixels in a row; and
    generating the mask as an array of addresses associated with the fluoroscopic image, the array of addresses corresponding to a plurality of black pixels that form a circumference of a x-ray disk defined in the fluoroscopic image.

27. The method of claim 26, wherein generating the mask as the array of addresses further comprises:
    generating a first integer equivalent to a starting address of a line of pixels in the background area of the fluoroscopic image; and
    generating a second integer equivalent to an ending address of the line of pixels in the background area.

28. The method of claim 26, further comprising:
    revising the array if a shift in the circumference of the x-ray disk defined in the fluoroscopic image is observed.

29. The method of claim 28, further comprising:
    determining if each address in the array is still associated with the location of a black pixel on the circumference of the fluoroscopic image; and
    shifting the address to a black pixel if the address identifies a non-black pixel.

30. The method of claim 24, further comprising:
    determining from the image an average value, an average slope, a highest value and a lowest value of non-black pixels in the background area of the image; and
    determining if the imaging device is active based on a comparison between a signature associated with the imaging device and the average value, the average slope, the highest value and the lowest value of non-black pixels in the background area of the image.

* * * * *